(12) United States Patent
Govari et al.

(10) Patent No.: US 12,324,669 B2
(45) Date of Patent: Jun. 10, 2025

(54) DETECTING LOCAL ACTIVATION SOURCE IN ATRIAL FIBRILLATION

(71) Applicant: BIOSENSE WEBSTER (ISRAEL) LTD., Yokneam (IL)

(72) Inventors: Assaf Govari, Haifa (IL); Vadim Gliner, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 415 days.

(21) Appl. No.: 18/085,648

(22) Filed: Dec. 21, 2022

(65) Prior Publication Data

US 2024/0206792 A1    Jun. 27, 2024

(51) Int. Cl.
*A61B 5/287* (2021.01)
*A61B 5/339* (2021.01)
*A61B 5/00* (2006.01)

(52) U.S. Cl.
CPC .............. *A61B 5/287* (2021.01); *A61B 5/339* (2021.01); *A61B 5/743* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 6,172,499 B1 | 1/2001 | Ashe |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,788,967 B2 | 9/2004 | Ben-Haim et al. |
| 6,892,091 B1 | 5/2005 | Ben-Haim et al. |
| 7,536,218 B2 | 5/2009 | Govari et al. |
| 7,756,576 B2 | 7/2010 | Levin |
| 7,848,787 B2 | 12/2010 | Osadchy |
| 7,869,865 B2 | 1/2011 | Govari et al. |

(Continued)

FOREIGN PATENT DOCUMENTS

| | | |
|---|---|---|
| CN | 105307561 A | 2/2016 |
| EP | 3331430 A4 | 3/2019 |

(Continued)

OTHER PUBLICATIONS

European Search Report for corresponding EPA No. 23218455.6 dated May 22, 2024.

*Primary Examiner* — Ankit D Tejani

(57) ABSTRACT

A system includes a processor and a display. The processor is configured to: (i) produce an electroanatomic (EA) map of a surface of the organ, the EA map specifying a propagation vector-field (PVF) indicative of propagation of an electrophysiological (EP) wave over at least the surface, (ii) select at least a region of the organ, (iii) calculate a gaussian integral of the PVF along a perimeter of at least a closed contour indicative of the selected region, and (iii) produce at the region, a tag indicative of the LAS, in case the calculated gaussian integral meets a criterion. The display is configured to display the EA map and at least the tag over the EA map.

18 Claims, 2 Drawing Sheets

(56) References Cited

U.S. PATENT DOCUMENTS

| | | |
|---|---|---|
| 8,456,182 B2 | 6/2013 | Bar-Tal et al. |
| 9,186,080 B2 | 11/2015 | Shuros et al. |
| 10,631,749 B2 | 4/2020 | Rubenstein |
| 2014/0330111 A1 | 11/2014 | Lichtenstein et al. |
| 2014/0336518 A1 | 11/2014 | Shuros et al. |
| 2015/0073246 A1* | 3/2015 | Chmiel ............... A61B 18/1492 600/374 |
| 2018/0235495 A1 | 8/2018 | Rubenstein |
| 2020/0187825 A1 | 6/2020 | Bar-Tal et al. |
| 2020/0390353 A1 | 12/2020 | Cohen et al. |
| 2021/0228139 A1 | 7/2021 | Rubenstein |
| 2022/0054070 A1 | 2/2022 | Honarbakhsh et al. |

FOREIGN PATENT DOCUMENTS

| | | |
|---|---|---|
| EP | 2994040 B1 | 8/2019 |
| EP | 3801341 A4 | 3/2022 |
| GB | 201915680 | 12/2019 |
| IL | 256956 A | 4/2022 |
| JP | 2016518937 A | 6/2016 |
| JP | 06069584 B2 | 2/2017 |
| JP | 2018525198 A | 9/2018 |
| JP | 06858188 B2 | 4/2021 |
| WO | WO 2014182842 A1 | 11/2014 |
| WO | WO 2017024107 A4 | 2/2017 |
| WO | WO 201915680 A1 | 1/2019 |
| WO | WO 2019236780 A1 | 12/2019 |
| WO | WO 2021084255 A1 | 5/2021 |

* cited by examiner

DETECTING LOCAL ACTIVATION SOURCE IN ATRIAL FIBRILLATION

FIELD OF THE DISCLOSURE

The present disclosure relates generally to medical devices, and particularly to methods and systems for detecting local activation sources in atrial fibrillation and displaying the local activation sources over a heart map.

BACKGROUND OF THE DISCLOSURE

Arrhythmias in a patient heart, such as atrial fibrillation, may be caused by various mechanisms, such as a local activation source. Sometimes, an electro-anatomical (EA) map of the heart is overloaded with vectors that indicate a location direction of propagation, which are indicative of sensed electrophysiologic (EP) signals, and may obstruct or hide a pattern indicative of the existence of a local activation source in the heart.

The present disclosure will be more fully understood from the following detailed description of the examples thereof, taken together with the drawings in which:

DETAILED DESCRIPTION OF EXAMPLES

Overview

Figure 1:
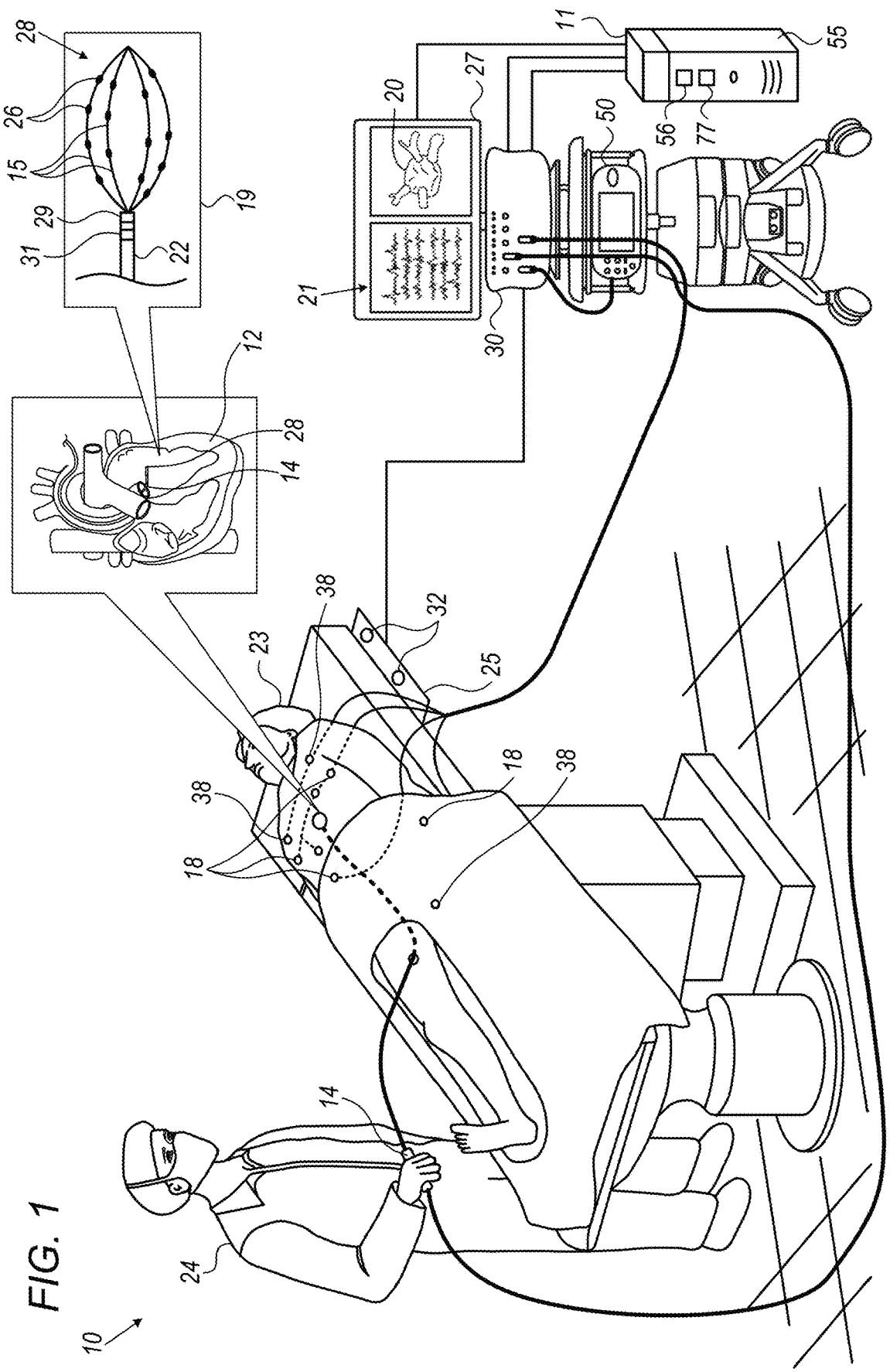
FIG. 1 is a schematic, pictorial illustration of a catheter-based electrophysiology mapping and ablation system, in accordance with an example of the present disclosure.

Arrhythmias may be caused by one or more local activation sources, such as a focal point, which may undesirably activate EP waves within the heart, in addition to the pacing of the sinus node of the heart. Electrophysiological (EP) procedures, such as tissue ablation, are used for treating arrhythmias in patient heart. For example, treating a local activation source (LAS) caused by atrial fibrillation in the patient heart requires insertion of a catheter having sensing electrodes into the atrium in order to sense EA signals on surfaces of at least the atrium, and carry out an electro-anatomical (EA) mapping of the atrium. The EA map specifies a propagation vector-field (PVF) indicative of propagation of one or more EP waves over one or more surfaces of the atrium and other chambers of the heart.

It is noted that such EA maps are displayed over the heart surface and typically comprise a large number of vectors (e.g., hundreds or thousands, depending on the mapping resolution) obtain by high density mapping of the heart. In case of arrhythmias, the heart may have multiple sources of local activation sources, which may appear chaotic to a physician. For example, atrial fibrillation may be caused when a plurality of LASs concurrently initiate activation, and thereby, may appear chaotic on the EA map. Therefore, the altered directions of vectors in the EA map may obstruct or hide a pattern of a LAS.

Examples of the present disclosure that are described below provide techniques for improved detection of LASs in an EA map having multiple PVFs.

In some examples, a catheter-based electrophysiology mapping and ablation system comprises a catheter having at least sensing electrodes configured to produce signals indicative of electrocardiogram (ECG) signals in patient heat. It is noted that various types of maps may be produced based on the signals received from the catheter, in the present example, analysis is carried out on velocity vectors shown on a voltage map measured on the heart surface. The catheter comprises one or more position sensors (e.g., magnetic based and impedance based) configured to produce position signals indicative of the position of the catheter and the electrodes while a physician moves the catheter along surfaces of the patient heart for performing EA mapping of the heart.

In some examples, the system further comprises a processor and a display device, also referred to herein as a display, for brevity. In the context of the present disclosure and in the claims, the terms "display" and "display device" refer to an electronic device that can be attached to a computer in order to present images or other sort of suitable information. Note that the display device may present the information received from the processor over a wire, or wirelessly. Based on the sensed ECG signals and the position signals, the processor is configured to produce an EA map of the chamber(s) of interest in the heart. The EA map specifies a PVF indicative of the propagation of one or more EP waves over one or more surfaces of the atrium of interest and other chambers of the heart. In other words, the PVF is indicative of the propagation velocity of the EP wave in at least a section of the heart. In alternative examples, the processor may produce or receive the EA map, which is acquired in advance, e.g., using another system.

In some examples, the processor is configured to select a region on the surface, and to define on the EA map a virtual closed contour, such as a circle or other closed contour that may typically be defined along a three-dimensional (3D) surface of the inner wall of the heart chamber, indicative of the selected region. Note that the region selection may be carried out solely by the processor or by the physician, or by both the processor and the physician assisting one another.

In some examples, the processor is configured to calculate a gaussian integral of the PVF along the perimeter of the circle (or any other suitable shape of the closed contour). Based on a typical pattern of vectors of a typical LAS (as described in detail in FIG. 2 below), a calculated gaussian integral having a value greater than zero, e.g., above a pre-defined threshold that may be defined based on empirical data, is indicative of the presence of a LAS within the closed contour. The processor is further configured to iteratively adjust at least one of the size, shape and location of the selected region and the corresponding virtual closed contour in order to pinpoint the location of the LAS. More specifically, the processor is configured to define, within the region surrounded by the virtual closed contour, a sub-region that meets the criterion, and thereby, provides a user with improved accuracy of the location of the LAS. Example implementations of these techniques are described in detail in FIGS. 2 and 3 below.

In some examples, the processor is configured to store an additional threshold (also referred to herein as a second threshold) indicative of the required area of the virtual closed loop. In case the area of the virtual closed loop is larger than the second threshold, the processor is configured to define another virtual closed loop that meets the required area of the virtual closed loop, e.g., to zoom into the closed loop area to provide more accurate location of the LAS. This second threshold may be selected and/or adjusted by a physician or clinical person. In response to obtaining a region having a virtual closed contour whose: (i) gaussian integral meets the criterion of the first threshold, and (ii) whose area is smaller than the second threshold, the processor is configured to produce a tag at the region, which is indicative of the detected LAS. Example implementations and variations of these techniques are described in further detail in FIGS. 2 and 3 below.

In some examples, the display is configured to display the tag over the EA map at the location of the selected region. Note that the virtual closed contour is used in the background for calculating whether or not the selected region has the LAS. Thus, the virtual closed contour is typically not displayed over the EA map of the heart.

The disclosed techniques enable fast and accurate detection and display of the presence and position of a LAS in patient heart, and therefore, improve the quality of focal-point treatment, and reduce the duration of ablation procedures.

System Description

FIG. 1 is a schematic, pictorial illustration of a catheter-based electrophysiology mapping and ablation system 10, in accordance with an example of the present disclosure. In the context of the present disclosure and in the claims, the term system refers to an integrated assemblage of hardware and/or software elements operating together to accomplish a prescribed end purpose described in detail below.

In some examples, system 10 includes multiple catheters, which are percutaneously inserted by a physician 24 through the patient's vascular system into a chamber or vascular structure of a heart 12. Typically, a delivery sheath catheter is inserted into the left or right atrium near a desired location in heart 12. Thereafter, one or more catheters can be inserted into the delivery sheath catheter so as to arrive at the desired location within heart 12. The plurality of catheters may include catheters dedicated for sensing Intracardiac Electrogram (IEGM) signals, catheters dedicated for ablating and/or catheters adapted to carry out both sensing and ablating. An example catheter 14 that is configured for sensing IEGM is illustrated herein. In some examples, physician 24 may place a distal tip 28 of catheter 14 in contact with the heart wall for sensing a target site in heart 12. Additionally, or alternatively, for ablation, physician 24 would similarly place a distal end of an ablation catheter in contact with a target site for ablating tissue intended to be ablated.

In other examples, the term "catheter" may refer to a tubular, flexible, surgical instrument, including, but not limited to, a sheath, having an end (e.g., distal tip 28) directed toward the treatment site in the patient, with a device at that end for delivering energy, such energy including, but not limited to, RF energy, microwaves, ultrasound, direct current, circulating heated fluid, radiant light, laser, and thermal energy.

Reference is now made to an inset 19 showing distal tip 28 of catheter 14. In the present example, catheter 14 includes one and preferably multiple electrodes 26 optionally distributed along and coupled to multiple splines 15 of a basket-shaped distal tip 28, which is connected to a shaft 22 of catheter 14. Electrodes 26 are configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

Reference is now made back to the general view of FIG. 1. In some examples, magnetic based position sensor 29 may be operated together with a location pad 25 including a plurality of (e.g., three) magnetic coils 32 configured to generate a plurality of (e.g., three) magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described, for example, in U.S. Pat. Nos. 5,391,199; 5,443,489; 5,558,091; 6,172,499; 6,239,724; 6,332,089; 6,484,118; 6,618,612; 6,690,963; 6,788,967; 6,892,091.

In some examples, catheter 14 includes a contact force sensor 31, which is configured to sense the contact force applied to tissue of heart 12 by distal tip 28, and to produce a signal indicative of the sensed contact force.

In some examples, system 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. This technique is also referred to herein as Advanced Current Location (ACL) and details of the impedance-based location tracking technology are described in U.S. Pat. Nos. 7,536,218; 7,756,576; 7,848,787; 7,869,865; and 8,456,182. In some examples, the magnetic based position sensing and the ACL may be applied concurrently, e.g., for improving the position sensing of one or more electrodes coupled to a shaft of a rigid catheter (e.g., a focal catheter), or to splines 15 or flexible arms at the distal tip of another sort of catheter, such as the PentaRay® or OPTRELL® catheters, available from Biosense Webster, Inc., 31A Technology Drive, Irvine, CA 92618.

In some examples, a recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

In some examples, system 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulse trains of pulsed-field ablation (PFA) energy, including monopolar or bipolar high-voltage DC pulses as may be used to effect irreversible electroporation (IRE), or combinations thereof. In the present example, catheter 14 does not include one or more ablation electrodes, for applying the RF energy and/or the pulse trains of PFA energy to tissue of the wall of heart 12. In other examples, at least one of electrodes 26 may be replaced with one or more ablation electrodes, respectively.

In some examples, patient interface unit (PIU) 30 is an interface configured to establish electrical communication between catheters, electrophysiological equipment, power supply and a workstation 55 for controlling the operation of system 10.

In the context of the present disclosure and in the claims, the term workstation refers to a position including a device or group of devices, which are equipped with capabilities for computer data processing in combination with audio and video interaction, and which are based upon or include a conventional desktop or portable computer. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

In some examples, workstation 55 includes a storage device and/or a processor 77 with suitable random-access memory, or storage with appropriate operating software stored therein, an interface 56 configured to exchange signals of data (e.g., between processor 77 and another entity of system 10, and/or with an entity external to system 10) and user interface capability. In the context of the present disclosure and in the claims, the term processor refers to a central processing unit in a computer for processing data and executing a program. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (4) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Figure 2:
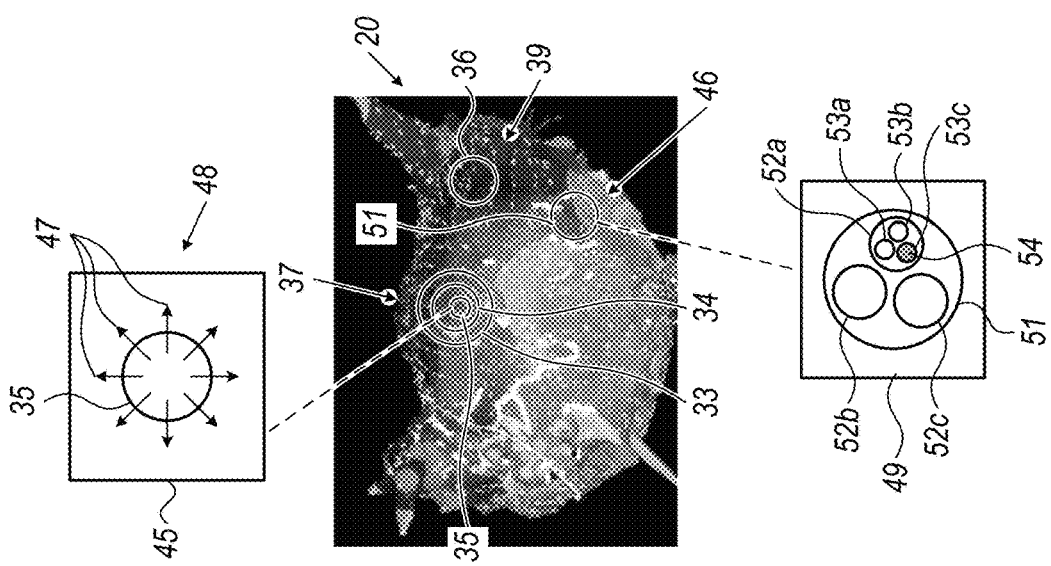
FIG. 2 is a schematic, pictorial illustration of virtual closed contours a tag displayed over a 3D anatomical map of a patient heart, in accordance with an embodiment of the present invention.

Identifying a Local Activation Source Caused by Atrial Fibrillation in Patient Heart FIG. 2 is a schematic, pictorial illustration of virtual closed contours (VCCs) 33, 34, 35, 36 (that may have a shape of circles or other sort of virtual closed contours) and a virtual closed contour (VCC) 51, and a tag 48 displayed over 3D electro anatomical map 20, in accordance with an embodiment of the present invention. In the context of the present disclosure and in the claims, the term "virtual closed contour" is also referred to herein as "closed contour." Anatomical map 20, which is also referred to herein as a map 20, for brevity, comprises a map of at least a portion of heart 12 presented over display device 27, as shown in FIG. 1 above.

In some examples, EA map 20 comprises one or more propagation vector-fields (PVFs) indicative of the propagation of one or more electrophysiological (EP) waves, respectively, over one or more surfaces of heart 12. In some cases, in atrial fibrillation of heart 12, propagation of the EP waves (e.g., cardiac action potential) may appear chaotic on map 20, and fractionated actional potentials may be observed by physician 24. For example, atrial fibrillation may be caused when a plurality of local activation points (LASs) e.g., focal points, concurrently initiate activation, and therefore, the PVF specified over map 20 may appear as a chaotic propagation having a random, or almost random, pattern. During an ablation procedure, physician 24 typically reviews the PVF of map 20 in order to identify the fibrillation source, such as one or more LASs. Subsequently, physician 24 may control system 10 to perform tissue ablation (e.g., RF ablation or PFA), at the identified LAS(s).

In some examples, processor 77 is configured to identify in EA map 20 one or more regions, such as regions 37 and 39, which are suspected to have arrhythmias caused by LASs. Additionally, or alternatively, physician 24 may define regions 37 and 39 as suspected locations in map 20 having LAS (s).

In some examples, processor 77 is configured to display, over map 20 at the position of regions 37 and 39, virtual closed contours (VCCs) indicative of regions 37 and 39. In the present example, the virtual closed contours of regions 37, 39 and 46 comprising VCCs 36 and 33, and VCC 51, respectively, which are displayed over map 20 at the respective positions of regions 39, 37 and 46, but in other examples, at least one of the closed contours may comprise any suitable shape and size other than a circle, such as but not limited to a virtual ellipse or any closed three dimensional contour along the wall of the heart chamber.

In some examples, processor 77 is configured to calculate a gaussian integral of the PVF along the perimeter of the respective virtual closed contours, e.g., along the perimeter of VCCs 33, 36 and VCC 51. It is noted that the velocity vectors of the PVF propagating from a local activation source, typically appears similar to that of an electrostatic field. Based on the flux theorem, the flux of the electric field out of an arbitrary closed surface, is proportional to the electric charge enclosed by the surface. More specifically, a closed contour that includes an electric charge that emits an electrostatic field will have given value of a gaussian integral along the surface of the close contour.

In some examples, based on the principle of the flux theorem, processor 77 is configured to calculate the gaussian integral of the PVF along the outer surface of VCCs 33, 36 and VCC 51, in order to identify whether or not a local activation source is present in an area within the area surrounded by VCCs 33, 36 and VCC 51. Based on the principle of the flux theorem, a calculated gaussian integral that exceeds a predefined threshold, is indicative of a local activation source within the respective region.

Reference is now made to an inset 49 showing VCCs defined in region 46. Note that the VCCs are used for the calculations of gaussian integral, and therefore, are typically not displayed over map 20 unless the user selects an option to display them. In the present example, map 20 comprises a voltage map, and the velocity vectors of map 20 are computed based on the voltage sensed by electrodes 26 of distal tip 28 shown in FIG. 1 above.

In some examples, processor 77 is configured to store: (i) a first threshold (e.g., the aforementioned predefined threshold) indicative of the presence of a LAS based on the calculated gaussian integral of the PVF along the perimeter of VCC 51, and (ii) a second threshold indicative of the required area of the closed contour in the selected region (e.g., region 46). In the present example, the first threshold may be zero or substantially near zero, and the diameter of a VCC for identifying a LAS is between about 0.5 cm and 2 cm. Therefore, the area of the closed contour and the second threshold may be between about 0.2 $cm^2$ and 4 $cm^2$. In other examples, the diameter range for identifying a LAS maybe different from the aforementioned range of about 0.5 cm and 2 cm, e.g., between about 0.1 cm and 3 cm. It is noted that the range is dictated by the size of the heart and the size of the LAS. Moreover, regions 37, 39 and 46 typically have a three-dimensional (3D) topography.

In some examples, the gaussian integral calculated along the perimeter of VCC 51 exceeds the first threshold, and therefore, is indicative of a LAS within the region surrounded by VCC 51. For example, the calculated gaussian integral is substantially above zero. However, the size of VCC 51 (e.g., an area of aa) is larger than the second threshold. In other words, it is required to pinpoint the accurate position of the LAS within the region surrounded by VCC 51.

In some examples, processor 77 is configured to define multiple VCCs 52*a*, 52*b* and 52*c* that cover most of or the entire region surrounded by VCC 51. In the present example, VCCs 52*a*-52*c* have a spherical shape, but in other examples, at least one of VCCs 52*a*-52*c* may have any other suitable shape, regular or irregular. Moreover, the size of the surfaces of VCCs 52*a*-52*c* is typically similar, but may have a different shape.

In some examples, processor 77 is configured to calculate the gaussian integral of the PVF along a perimeter of each of VCCs 52*a*, 52*b* and 52*c*, and to compare each of the calculated gaussian integrals to the first threshold. In the present example, the calculated gaussian integrals of VCCs 52*b* and 52*c* are approximately zero or near zero and therefore, are smaller than the first threshold. The calculated gaussian integral of VCC 52*a* exceeds the first threshold, e.g., is clearly and/or significantly above zero which is indicative that the LAS is located within the region surrounded by VCC 52*a*. However, the size of VCC 52*a* does not provide the needed resolution, e.g., as selected by the physician or the default resolution stored in memory, e.g., is larger than the second threshold. In other words, a smaller-size VCC must be defined within the region surrounded by VCC 52*a*, in order to identify the location of the LAS in the required accuracy. Note that physician 24 may use the location of the LAS for planning a treatment, such as tissue ablation. Therefore, it is important to identify the location of the LAS with sufficient accuracy so as to improve the quality of the treatment.

In some examples, processor 77 is configured to continue the iterative process of identifying the accurate position of the LAS by defining multiple VCCs 53*a*, 53*b* and 53*c* within the region surrounded by VCC 52*a*. In the present example, VCCs 53*a*-53*c* have a spherical shape, but in other examples, at least one of VCCs 53*a*-53*c* may have any other suitable shape, regular or irregular. Moreover, the size of VCCs 53*a*-53*c* is typically similar, but may have a different shape. In other examples, the size VCCs 53*a*-53*c* may not be similar.

In some examples, processor 77 is configured to calculate the gaussian integral of the PVF along a perimeter of VCCs 53*a*, 53*b* and 53*c*, and to compare each of the calculated gaussian integrals to the first threshold. In the present example, the calculated gaussian integrals of VCCs 53*a* and 53*b* are smaller than the first threshold, e.g., approximately zero and calculated gaussian integral of VCC 53*c* exceeds the first threshold (greater than zero), which is indicative that the LAS is located within the region surrounded by VCC 53*c*. The size of VCC 53*c* is smaller than the second threshold, and therefore, VCC 53*c* meets the criterion for containing the LAS at a sufficient positioning accuracy.

In some examples, processor 77 is configured to produce a tag 54 at the position of VCC 53*c* in response to identifying that: (i) the calculated gaussian integral of the PVF along the outer surface of VCC 53*c* exceeds the first threshold, and (ii) the region surrounded by VCC 53*c* is smaller than the second threshold. The iterative process described above may be implemented in system 10 for identifying the presence and the accurate location of a LAS in heart 24. Moreover, display device 27 is configured to display tag 54 over map 20 in order to provide physician 24 with the presence and the accurate location of the LAS in heart 12. In the present example, VCCs 53*a* and 53*b* do not contain the LAS, and therefore, appear as unfilled circles, whereas tag 54 and VCC 53*c* are overlaid and appear as a solid (i.e., filled) circles. In other examples, tag 54 may comprise any suitable type of marker, other than a solid sphere. An example implementation of another sort of tag is shown in FIG. 2 and is described in detail below.

Reference is now made back to the general view of FIG. 2. In the present example, the calculated gaussian integral along the perimeter of VCC 36 is substantially smaller than the predefined threshold (e.g., approximately zero), and therefore, region 39 does not appear to have a LAS. The deviation from the predefined threshold in the gaussian integral along the perimeter of VCC 33 may be cause by various reasons, for example, in case region 37 comprises the LAS and additional vector fields located out of the LAS.

In the context of the present disclosure and in the claims, the terms "about" or "approximately" for any numerical values or ranges indicate a suitable dimensional tolerance that allows the part or collection of components to function for its intended purpose as described herein.

In some examples, in order to check whether region 37 may have a LAS, processor 77 is configured to calculate the gaussian integral of the PVF along a perimeter of VCC 33. By using the same technique described in inset 49 above, processor 77 is configured to obtain an indication of the presence of a LAS within the area enclosed in VCC 33, when the calculated value of the gaussian integral is approximately similar to or larger than the first threshold. However, perimeter of VCC 33 may be larger than the second threshold and in addition to the LAS, the area enclosed by VCC 33 may comprise additional vectors that are not part of the LAS. For example, the LAS may have a diameter between about 0.5 cm and 2 cm, and VCC 33 may have a diameter of about 6 cm. In this example, it is required to reduce the volume surrounding the LAS, so as to pinpoint the exact location of the LAS within the volume surrounded by VCC 33.

In some examples, processor 77 is configured to adaptively modify at least one of: the size, the shape, and the location of the region intended to be checked for being suspected to have a LAS. In one example, in region 39, in response to identifying that the calculated gaussian integral of the PVF along the perimeter of VCC 36 is approximately zero (or having a value substantially smaller than the first threshold), processor 77 is configured to remove VCC 36 from region 39 and stop calculating gaussian integrals in this region. In the example described above, in region 37 the calculated gaussian integral of the PVF along the perimeter of VCC 33 is approximately similar to or larger than the first threshold. In this example, processor 77 is configured to: (i) define within region 37, a subregion and an additional virtual closed contour at the location of the subregion, and (ii) calculate an additional gaussian integral of the additional virtual closed contour at the subregion.

In the example of FIG. 2, processor 77 is configured to: (i) define a VCC 34 (that may be concentric or non-concentric with and smaller than VCC 33) at the location of the subregion within region 37, and (ii) calculate the gaussian integral of the PVF along the perimeter of VCC 34. Note that in case the LAS is located in both VCCs 33 and 34, the calculated gaussian integral of the PVF along the outer perimeter of VCC 34 is expected to be larger compared to that of VCC 33.

In case the calculated gaussian integral of the PVF along the perimeter of VCC 34 is approximately similar to or larger than the threshold, processor 77 is configured to: (i) define a closed contour, such as VCC 35 (smaller than VCC 34) located within the subregion of region 37, and (ii)

calculate the gaussian integral of the PVF along the perimeter of VCC 35. In this example, in case the calculated gaussian integral of the PVF along the perimeter of VCC 35 exceeds the threshold, this is indicative that the LAS resides within and fills a significant portion of the region surrounded by VCC 35.

Reference is now made to an inset 45. In some examples, vectors 47, which are the propagation vectors of the PVF at the location of VCC 35, are distributed uniformly along the perimeter of VCC 35, and are pointing outwards. In response to identifying that (i) the calculated gaussian integral of the PVF along the perimeter of VCC 35 exceeds the first threshold and (ii) the volume surrounded by VCC 35 is smaller than the second threshold, processor 77 is configured to display at the location of VCC 35, a tag 48, which is indicative of the presence and location of the LAS.

Reference is now made back to the general view of FIG. 2, which is an electroanatomic (EA) map 20 that represents the anatomy of an actual organ (which map can be generated by a Carto 3® mapping system manufactured by Biosense Webster Inc.) and overlaid with voltage signals collected by a mapping or recording catheter such as catheter 28 shown in FIG. 1 above. In some examples, based on the outcome described above, display device 27 is configured to display tags 48 and 54 over map 20 to physician 24 (or any other user).

To summarize the examples of FIG. 2, processor 77: (i) receives (from a user) or (automatically) selects regions 37, 39 and 46, (ii) defines VCCs (e.g., VCCs 33 and 36, and VCC 51), respectively, (iii) calculates the gaussian integral of the PVF along the outer perimeters of each VCC, (iv) in case the calculated gaussian integral is below the first threshold (e.g., in VCC 36), the respective region (e.g., region 39) does not contain a LAS, (v) in case the calculated gaussian integral is approximately similar to, or exceeds the first threshold (e.g., in VCC 33 and VCC 51) and the perimeter thereof exceeds the second threshold, processor 77 is configured to define one or more subsequent closed contours (e.g., VCCs 34 and 35 and VCCs 52a-52c and 53a-53c) within the regions surrounded by VCC 33 and VCC 51, respectively. This iterative process continues until processor 77 obtains one or more VCC (e.g., VCC 35 and VCC 53c), which contain the respective LASs and are sufficiently small to provide physician with the presence and accurate location of the respective LASs within heart 12. Subsequently, processor 77 produces a suitable marker (e.g., tags 48 and 54), which are presented by display device 27 over map 20 at the locations of the respective VCCs (e.g., VCC 35 and VCC 53c). Note that by default, the VCCs and circles are not presented over map 20, however, physician 24 or any other user may optionally control processor 77 to present at least one of the VCCs and/or circles over map 20.

Figure 3:
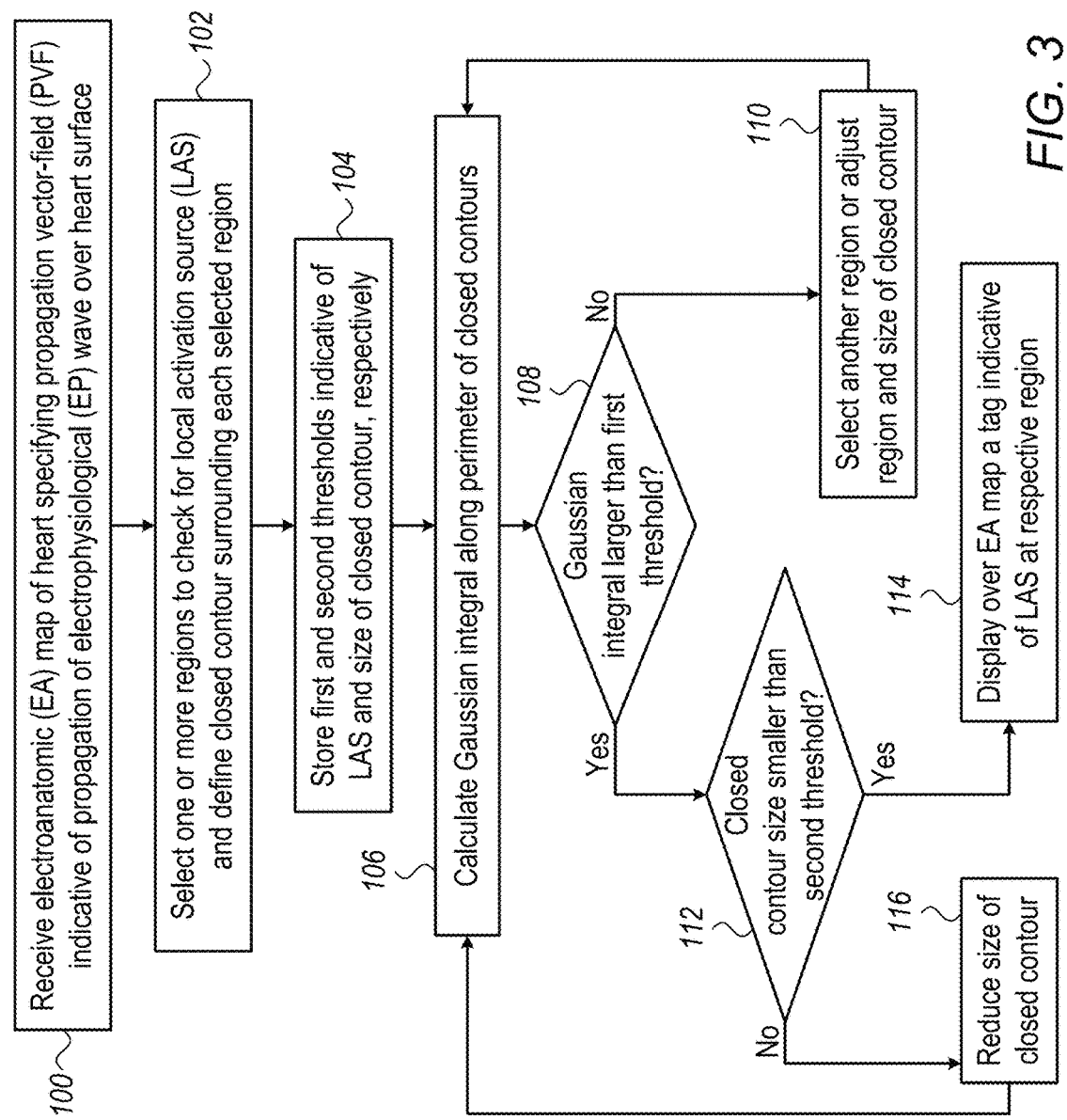
FIG. 3 is a flow chart that schematically illustrates a method for detecting and displaying a local activation source in the 3D anatomical map of the heart of FIG. 2, in accordance with an example of the present disclosure.

FIG. 3 is a flow chart that schematically illustrates a method for detecting and displaying one or more LASs over map 20 of heart 12, in accordance with an example of the present disclosure.

The method begins at a map receiving step 100, with processor 77 producing or receiving EA map 20, which is a map of voltages sensed by electrodes 26 in heart 12. Based on the sensed voltages processor 77 calculates velocity vectors and produces map 20, which is specifying the PVF indicative of the propagation of the EP wave over one or more surfaces of heart 12, as described in detail in FIG. 2 above.

At a region selection step 102, one or more regions, such as regions 37, 39 and 46 are selected to check for LASs. As described in detail in FIG. 2 above, VCCs (e.g., VCCs 33 and 36, and VCC 51) are defined and virtually positioned to surround regions 37, 39 and 46, respectively. Note that regions 37, 39 and 46 may be selected by physician 24, or by processor 77, or by any suitable combination thereof (e.g., physician 24 selects a large area, and processor 77 selects at least one of regions 37, 39 and 46 within the large area. Additionally, or alternately, processor 77 may carry out the entire selection process. For example, processor 77 may select areas that produce fractioned signals.

In other examples, at least two of the selection regions and respective VCCs may comprise overlapping areas. Optionally, the entire area of map 20 may be covered with VCCs. Moreover, the VCCs are defined by processor 77 responsively to the selection of regions 37, 39 and 46, and the defined VCC are typically 3D, but may also be 2D.

At a threshold storing step 104, which may also be carried out before step 100 or before step 102, processor 77 stores and holds the first and second thresholds indicative of LAS criterion and the required size of the closed contour, respectively, as described in detail in FIG. 2 above.

At a gaussian integral calculation step 106, processor 77 calculates the gaussian integral of the PVF along the perimeter of one or more VCCs (and spheres or circles) defined (and optionally displayed) in map 20, in the present example, VCCs 36 and 35 and VCC 51 defined in selected regions 39, 37 and 46, respectively, as described in more detail in FIG. 2 above.

At a first decision step 108, processor 77 checks whether the gaussian integral of the PVF, which is calculated along the perimeter of VCCs 36 and 35, and VCC 51, is approximately similar to or larger than the first threshold. As described in the example of FIG. 2 above, the calculated gaussian integral of the PVF along the perimeter of VCC 36 is substantially smaller than the first threshold (e.g., having a value of approximately zero), which is indicative that region 39 does not contain a LAS. Moreover, the calculated gaussian integral of the PVF along the perimeter of both VCC 33 and VCC 51 are approximately similar to, or larger than the first threshold, which is indicative that both regions 37 and 46 may contain one or more LASs.

At a region adjustment step 110, because the calculated gaussian integral of the PVF along the perimeter of VCC 36 is substantially smaller than the first threshold, processor 77 infers that region 39 does not have a LAS. Thus, processor 77 stops the definition of VCCs at region 39, and may define one or more VCCs at other regions on map 20. Subsequently, the method loops back to step 106, in which processor 77 calculates the gaussian integral of the PVF along the perimeter of the one or more VCCs defined at the other region. Additionally, or alternatively, in case the calculated gaussian integral of the PVF along the perimeter of VCC 36 is slightly smaller than the first threshold, processor 77 may define smaller VCCs within region 39, and the method loops back to step 106 for calculating the gaussian integral of the PVF along the perimeter of the one or more VCCs.

As described in step 108 above, in the example of FIG. 2 above, the calculated gaussian integral of the PVF along the perimeter of each of VCC 33 and VCC 51 is approximately similar to or larger than the first threshold, which is indicative that each of regions 37 and 46 may contain one or more LASs. In this example, the method proceeds to a second decision step 112, in which processor 77 compare between the size of each of the VCCs (e.g., VCC 33 and VCC 51) and the second threshold.

In the example shown in FIG. 2 above, the size of each of VCC 33 and VCC 51 is larger than the second threshold, and the method proceeds to a VCC redefinition step 116 with processor 77 defining: (i) VCC 34 within the region enclosed by VCC 33, and (ii) VCCs 52a-52c within the region surrounded by VCC 51, and the method loops back to step 106 for an iteration of calculating the gaussian integral of the PVF along perimeter of VCC 34 and VCCs 52a-52c. As described in detail in FIG. 2 above, at step 108 the calculated gaussian integral of the PVF along the perimeter of each of VCC 34 and VCC 52a is larger than the first threshold. However, at step 112 the size of each of VCC 34 and VCC 52a is larger than the second threshold, and the method proceeds to step 116 with processor 77 defining: (i) VCC 35 within the region surrounded by VCC 34, and (ii) VCCs 53a-53c within the region surrounded by VCC 52a, and the method loops back to step 106 for an additional iteration.

In some examples, at step 108 the calculated gaussian integral of the PVF along the perimeter of each of VCC 35 and VCC 53c is larger than the first threshold. Moreover, at step 112 the size of each of VCC 35 and VCC 53c is smaller than the second threshold. Thus, the method proceeds to a tag display step 114 that concludes the method. At step 114, processor 77 produces tags 48 and 54, which are indicative of the location of LASs at regions 37 and 46, respectively, and display device 27 presents tags 48 and 54 over regions 37 and 46, respectively. Note that tags 48 and 54 may have similar marks, or different marks, as shown in the example of FIG. 2.

In some examples, by adaptively modifying at least one of the size, the shape, and the location of the region and corresponding VCCs, processor 77 is configured to reach a gaussian integral that is larger than the first threshold, and thereby, processor 77 provides physician 24 with the presence and accurate location of one or more LASs over map 20 of heart 12.

In some examples, the method may be carried out in a fully automated manner, such that processor 77: (i) selects one or more candidate regions, (ii) defines one or more VCCs in each of the selected regions, and calculates the gaussian integral of the PVF along the outer surface of each respective VCC, and (iii) displays tags 48 and 54 at the position of VCCs 35 and 53c, respectively.

Additionally, or alternatively, the selection of one or more of the candidate regions may be carried out by physician 24, and the remaining steps of the method described above are carried out by processor 77. Moreover, processor 77 is further configured to: (i) receive interventions from physician 24 for adjusting at least one of the position, size, and shape of one or more of the virtual closed contours, and (ii) proceed with the operations described in steps 104-116 above.

Although the examples described herein mainly address detection and display of LASs in patient heart, the methods and systems described herein can also be used in other applications, such as in detecting and displaying an indication of other suitable medical phenomena based on suitable signals received from any suitable organ of a patient.

Example 1

A system (10) for detecting a local activation source (LAS) in an organ, the system includes: (a) a processor (77), which is configured to: (i) produce an electroanatomic (EA) map (20) of a surface of an organ (12), the EA map specifying a propagation vector-field (PVF) indicative of propagation of an electrophysiological (EP) wave over at least the surface, (ii) select at least a region (37, 39, 46) of the organ, (iii) calculate a gaussian integral of the PVF along a perimeter of at least a closed contour (33, 34, 35, 36, 51, 52a, 52b, 52c, 53a, 53b, 53c) indicative of the selected region, and (iii) produce at the region, a tag (48, 54) indicative of the LAS, in case the calculated gaussian integral meets a criterion, and (b) a display (27), which is configured to display the EA map and at least the tag over the EA map.

Example 2

The system according to Example 1, wherein the criterion comprises presence of the LAS at the selected region, and wherein the processor is configured to store a threshold indicative of the presence of the LAS, and to produce the tag in case the calculated gaussian integral exceeds the threshold.

Example 3

The system according to Example 2, wherein the processor is configured to store an additional threshold indicative of an area of the closed contour in the selected region, and wherein, in case the area exceeds the additional threshold, the processor is configured to: (i) produce, within the area of the closed contour, a subsequent closed contour (SCC) having a reduced area, and (ii) calculate a subsequent gaussian integral of the PVF along a subsequent perimeter of the SCC.

Example 4

The system according to Examples 1-3, wherein the at least closed contour comprises first and second closed contours having first and second surfaces, respectively, and wherein the processor is configured to calculate a first gaussian integral of the PVF along the first perimeter, and a second gaussian integral of the PVF along the second perimeter.

Example 5

The system according to Example 4, wherein the processor is configured to calculate the second gaussian integral after calculating the first gaussian integral.

Example 6

The system according to Example 4, wherein the processor is configured to calculate the first and second gaussian integrals simultaneously.

Example 7

The system according to Examples 1-3, wherein the organ comprises a heart, and the tag is indicative of the LAS in the heart.

Example 8

The system according to Examples 1-3, wherein the closed contour comprises a virtual closed contour, which is not displayed over the EA map.

Example 9

The system according to Examples 1-3, wherein the display is configured to display the closed contour over the selected region of the EA map.

Example 10

A method for detecting a local activation source (LAS) in an organ (12), the method comprising:
producing an electroanatomic (EA) map (20) of a surface of the organ, the EA map specifying a propagation vector-field (PVF) indicative of propagation of an electrophysiological (EP) wave over at least the surface;
selecting at least a region (37, 39, 46) of the organ, and calculating a gaussian integral of the PVF along perimeter of at least a closed contour (33, 34, 35, 36, 51, 52a, 52b, 52c, 53a, 53b, 53c) indicative of the selected region;
producing at the region, a tag (48, 54) indicative of the LAS, in case the calculated gaussian integral meets a criterion; and
displaying the EA map and at least the tag over the EA map.

Example 11

The method according to Example 10, wherein the criterion comprises presence of the LAS at the selected region, and wherein producing the tag comprises storing a threshold indicative of the presence of the LAS, and producing the tag in case the calculated gaussian integral exceeds the threshold.

Example 12

The method according to Example 11, and comprising storing an additional threshold indicative of an area of the closed contour in the selected region, and in case a size of the area exceeds the additional threshold, the method comprising: (i) producing, within the area of the closed contour, a subsequent closed contour (SCC) having a reduced size of the area, and (ii) calculating a subsequent gaussian integral of the PVF along a subsequent perimeter of the SCC.

Example 13

The method according to Examples 10-12, wherein the at least closed contour comprises first and second closed contours having first and second surfaces, respectively, and wherein calculating the gaussian integral comprises calculating (i) a first gaussian integral of the PVF along the first perimeter, and (ii) a second gaussian integral of the PVF along the second perimeter.

Example 14

The method according to Example 13, wherein the second gaussian integral is calculated after the first gaussian integral.

Example 15

The method according to Example 13, the first and second gaussian integrals are calculated simultaneously.

Example 16

The method according to Examples 10-12, wherein the organ comprises a heart, and the tag is indicative of the LAS in the heart.

Example 17

The method according to Examples 10-12, wherein the closed contour comprises a virtual closed contour which is not displayed over the EA map.

Example 18

The method according to Examples 10-12, and comprising displaying the closed contour over the selected region of the EA map.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for detecting a local activation source (LAS) in an organ, the system comprising:
a processor, which is configured to: (i) produce an electroanatomic (EA) map of a surface of the organ, the EA map specifying a propagation vector-field (PVF) indicative of propagation of an electrophysiological (EP) wave over at least the surface, (ii) select at least a region of the organ, (iii) calculate a gaussian integral of the PVF along a perimeter of at least a closed contour indicative of the selected region, and (iii) produce at the region, a tag indicative of the LAS, in case the calculated gaussian integral meets a criterion; and
a display, which is configured to display the EA map and at least the tag over the EA map.

2. The system according to claim 1, wherein the criterion comprises presence of the LAS at the selected region, and wherein the processor is configured to store a threshold indicative of the presence of the LAS, and to produce the tag in case the calculated gaussian integral exceeds the threshold.

3. The system according to claim 2, wherein the processor is configured to store an additional threshold indicative of an area of the closed contour in the selected region, and wherein, in case the area exceeds the additional threshold, the processor is configured to: (i) produce, within the area of the closed contour, a subsequent closed contour (SCC) having a reduced area, and (ii) calculate a subsequent gaussian integral of the PVF along a subsequent perimeter of the SCC.

4. The system according to claim 1, wherein the at least closed contour comprises first and second closed contours having first and second surfaces, respectively, and wherein the processor is configured to calculate a first gaussian integral of the PVF along the first perimeter, and a second gaussian integral of the PVF along the second perimeter.

5. The system according to claim 4, wherein the processor is configured to calculate the second gaussian integral after calculating the first gaussian integral.

6. The system according to claim 4, wherein the processor is configured to calculate the first and second gaussian integrals simultaneously.

7. The system according to claim 1, wherein the organ comprises a heart, and the tag is indicative of the LAS in the heart.

8. The system according to claim 1, wherein the closed contour comprises a virtual closed contour, which is not displayed over the EA map.

9. The system according to claim 1, wherein the display is configured to display the closed contour over the selected region of the EA map.

10. A method for detecting a local activation source (LAS) in an organ, the method comprising:
producing an electroanatomic (EA) map of a surface of the organ, the EA map specifying a propagation vector-field (PVF) indicative of propagation of an electrophysiological (EP) wave over at least the surface;
selecting at least a region of the organ, and calculating a gaussian integral of the PVF along perimeter of at least a closed contour indicative of the selected region;
producing at the region, a tag indicative of the LAS, in case the calculated gaussian integral meets a criterion; and
displaying the EA map and at least the tag over the EA map.

11. The method according to claim 10, wherein the criterion comprises presence of the LAS at the selected region, and wherein producing the tag comprises storing a threshold indicative of the presence of the LAS, and producing the tag in case the calculated gaussian integral exceeds the threshold.

12. The method according to claim 11, and comprising storing an additional threshold indicative of an area of the closed contour in the selected region, and in case a size of the area exceeds the additional threshold, the method comprising: (i) producing, within the area of the closed contour, a subsequent closed contour (SCC) having a reduced size of the area, and (ii) calculating a subsequent gaussian integral of the PVF along a subsequent perimeter of the SCC.

13. The method according to claim 10, wherein the at least closed contour comprises first and second closed contours having first and second surfaces, respectively, and wherein calculating the gaussian integral comprises calculating (i) a first gaussian integral of the PVF along the first perimeter, and (ii) a second gaussian integral of the PVF along the second perimeter.

14. The method according to claim 13, wherein the second gaussian integral is calculated after the first gaussian integral.

15. The method according to claim 13, the first and second gaussian integrals are calculated simultaneously.

16. The method according to claim 10, wherein the organ comprises a heart, and the tag is indicative of the LAS in the heart.

17. The method according to claim 10, wherein the closed contour comprises a virtual closed contour which is not displayed over the EA map.

18. The method according to claim 10, and comprising displaying the closed contour over the selected region of the EA map.

* * * * *